United States Patent [19]

Tagawa et al.

[11] 4,241,462
[45] Dec. 30, 1980

[54] DIAPER COVER TYPE GARMENT

[75] Inventors: Hiroshi Tagawa; Kenichiro Kurisu, both of Fukuoka, Japan

[73] Assignee: Nishiki Co., Ltd., Fukika, Japan

[21] Appl. No.: 514,027

[22] Filed: Oct. 11, 1974

[51] Int. Cl.³ .............................................. A41B 9/00
[52] U.S. Cl. ...................................... 2/406; 128/284
[58] Field of Search ............... 2/224 A, 224, 225, 226, 2/DIG. 6; 128/284, 288, 287

[56] References Cited

U.S. PATENT DOCUMENTS

| 2,530,719 | 11/1950 | Neal | 128/284 |
| 3,077,193 | 2/1963 | Mann | 2/406 |
| 3,828,785 | 8/1974 | Gamm et al. | 128/288 |

FOREIGN PATENT DOCUMENTS

| 1932606 | 1/1971 | Fed. Rep. of Germany | 2/406 |
| 1297739 | 5/1962 | France | 128/288 |

*Primary Examiner*—H. Hampton Hunter

*Attorney, Agent, or Firm*—James C. Wray

[57] ABSTRACT

A diaper cover type garment has a first panel with lateral edges which curve from a maximum near a rearward edge to an intermediate minimum corresponding to a between leg portion and which curve outward to a front edge. A second panel slightly and uniformly tapers from a rear edge connection to a front edge connection. The second panel is formed of an inward fabric layer and a waterproof sheet layer facing the first panel. The first and second panels are stitched downward along lateral edges of the second panel in a back portion of the garment.

Fasteners are arranged in sloping lines on a front portion of the garment, and complementary fasteners are mounted within rearward corners of the front panel. Hook and loop fasteners are mounted on the panels without reinforcement. Reinforcement panels are provided on the inside of the first panel with snap type fasteners.

9 Claims, 7 Drawing Figures

DIAPER COVER TYPE GARMENT

BACKGROUND OF THE INVENTION

Diaper cover type garments are well known. The conventional diaper cover type garment is waterproof pants with elasticized leg and body openings. Usually, the waterproof pants are made of a waterproof sheet material. In some occasions, the waterproof diaper cover pants are made of a waterproof sheet material covered outwardly by a decorative fabric. In those forms of diaper type covers, the elasticized leg and waistbands may be unduly restrictive on body portions of the infant wearer. The waterproof sheet tends to hold the body fluids inward toward the skin of the wearer, causing irritation to the wearer. In prior art devices no attempt is made to channel and direct body fluids away from the source and to distribute the fluid uniformly through the diaper type garment while preventing egress toward outer clothing of the wearer.

SUMMARY OF THE INVENTION

The present invention provides a diaper cover with a loosely connected first and second outer and inner panels. The outer panel is formed as a lower torso body fitting garment, and the inner panel is loosely connected to the outer panel in a front-to-rear through-the-leg direction. The second panel is connected to the first panel near forward and rearward edges. The second panel is formed in a preferred embodiment of a waterproof sheet which faces the first panel and of an inward facing fabric layer. The two layers of the second panel are joined around all edges in a preferred embodiment, and middle portions of the panels are loosely juxtaposed. The second panel thereby forms a forward to rearward channel for retaining body fluids laterally inward and directing body fluids forward and rearward to be absorbed substantially uniformly in a diaper. The inner layer of the second panel is made of an absorbent wicking material, preferably a terry cloth or flannel type material to aid in the absorption and retention of the body fluids in the central second panel and to aid in the redistribution of the body fluids to other distant portions of the diaper along the second panel.

The outer first panel is constructed of a porous absorbent material such as a terry cloth or a knitted material to absorb and evaporate moisture.

In a preferred embodiment of the invention, the second panel is stitched to the first panel only along the front and rear edges. In the preferred embodiment, the second panel is made of a tapering form with a wide portion at the rear edge and a slightly narrower front edge portion with straight slightly sloping lateral walls.

The first panel is made with relatively straight forward and rearward edges being uniformly curved at ends thereof into lateral edges with curved forward and rearward corners. The first panel has a relatively wide portion near the rearward edge, and the lateral edges curve inward to a narrow portion of a width about the same as the width of the second panel in a medial portion which fits between legs of a baby. A front portion of the first panel is slightly wider than the medial portion, being formed with uniformly curving lateral edges.

Fasteners are arranged on an outer surface of the front portion remote from the second panel. In a preferred embodiment, the fasteners on the front portion are arranged in a sloping manner and are positioned inward from the front edge and from the lateral edges.

Complementary fasteners are mounted in positions substantially in the extreme remote sections in the area of intersection of the rear and lateral edges. In one embodiment, the fasteners on the front portion comprise elongated strips of loop-type fasteners, and the complementary fasteners in the rear portion comprise complementary hooks arranged in relatively short strips. The hook strips may be connected to the loop strips at any position to form the desired waist size and leg opening sizes.

The loop strips may be stitched through the front portion of the first outer panel and through the underlying portion of the second inner panel.

When snap type fasteners are employed, snaps may be arranged in sloping rows along the front outer portion of the first panel, and corresponding snaps may be arranged in remote areas of the rear portion of the first outer panel. In a preferred embodiment, when snaps are employed, a reinforcing panel is stitched across the front portion between the first and second panels, and reinforcing corner panels are stitched in corners of the rear portion.

In a preferred embodiment of the invention, lateral edges of the second panel are stitched to the first panel downward along lines extending over a rear area of the first panel to provide a further control of the positioning of the panel while in use.

One object of the invention is the provision of a diaper cover type garment having another panel configured for mounting on an infant's body and having an inner panel extending from a medial portion of a rearward edge of the outer panel to a medial portion of a forward edge of the outer panel and being joined to the outer panel substantially only at the rearward and forward edges.

Another object of the invention is the provision of a garment comprising a first panel having a rearward edge and a forward edge and having lateral edges interconnecting the rearward and forward edges and further comprising a second panel having rearward and forward edges and having lateral edges interconnecting the rearward and forward edges of the second panel, the second panel being attached to the first panel with at least portions of the lateral edges of the second panel being spaced from the first panel, and means joining the first panel at positions near rearward and forward edges with an outer side of the first panel opposite the second panel whereby the first panel is formed and held as a garment with the second panel facing a body of the wearer.

Another object of the invention is the provision of a garment as described wherein the second panel comprises a waterproof sheet.

Another object of the invention is the provision of the described garment wherein the second panel comprises a waterproof sheet layer facing the first panel and a fabric layer facing opposite the first panel.

The invention has as another object the provision of a diaper cover type garment wherein the first outer and second inner panels are longitudinally coextensive between the forward and rearward edges and wherein the first and second panels are joined substantially only at the forward and rearward edges.

The invention has as another object the provision of the diaper cover type garment wherein portions of lateral edges of the second panel are joined to the first panel near the rearward edge of the first panel.

Another object of this invention is the provision of the garment as described wherein portions of lateral edges of the second panel are positioned inward from portions of lateral edges of the first panel and wherein the lateral edges of the first panel are sloped inward toward a medial portion of the first panel thereby forming a medial narrow portion of the first panel.

A further object of the invention is the provision of a pants type garment wherein lateral edges of a second inner loose panel are substantially straight and wherein the lateral edges of the second panel are positioned near medial inward portions of curved lateral edges of a first outer panel.

Another object of the invention is the provision of the same garment wherein the second panel uniformly tapers inward from a major dimension on the rear edges to a lesser dimension on the front edges.

This invention has as a further object the provision of the garment as described generally where fasteners are provided on an outer face of the first panel, positioned inward from the forward edge and wherein complementary fasteners are mounted on an inner face of the first panel near intersections of the rearward and lateral edges, whereby the garment is formed by covering the first panel about the second panel and covering rearward corners of the second panel over a forward portion of the first panel and joining the complementary fasteners.

The invention has as another object the provision of a diaper cover type garment wherein complementary fasteners comprise elongated strips of loop-type fasteners attached to one face of a first panel and relatively short strips of hook-type fasteners attached to another face of the first panel.

Another object of the invention is the provision of a diaper cover type garment with loosely connected first outer and second inner panels further comprising a front reinforcing panel connected to the first panel along the front edge and between portions of the lateral edges and wherein fasteners are mounted on the first panel and are connected to the reinforcing panel, and further comprising corner reinforcing panels connected to the first panel at corners of the rearward and lateral edges and wherein the complementary fasteners are mounted in the first panel and are connected to the corner reinforcing portions.

These and further objects and features of the invention are apparent in the disclosure which includes the foregoing and ongoing specification, which is completed by the claims, and the drawings.

DETAILED DESCRIPTION OF THE DRAWINGS

Figure 1:
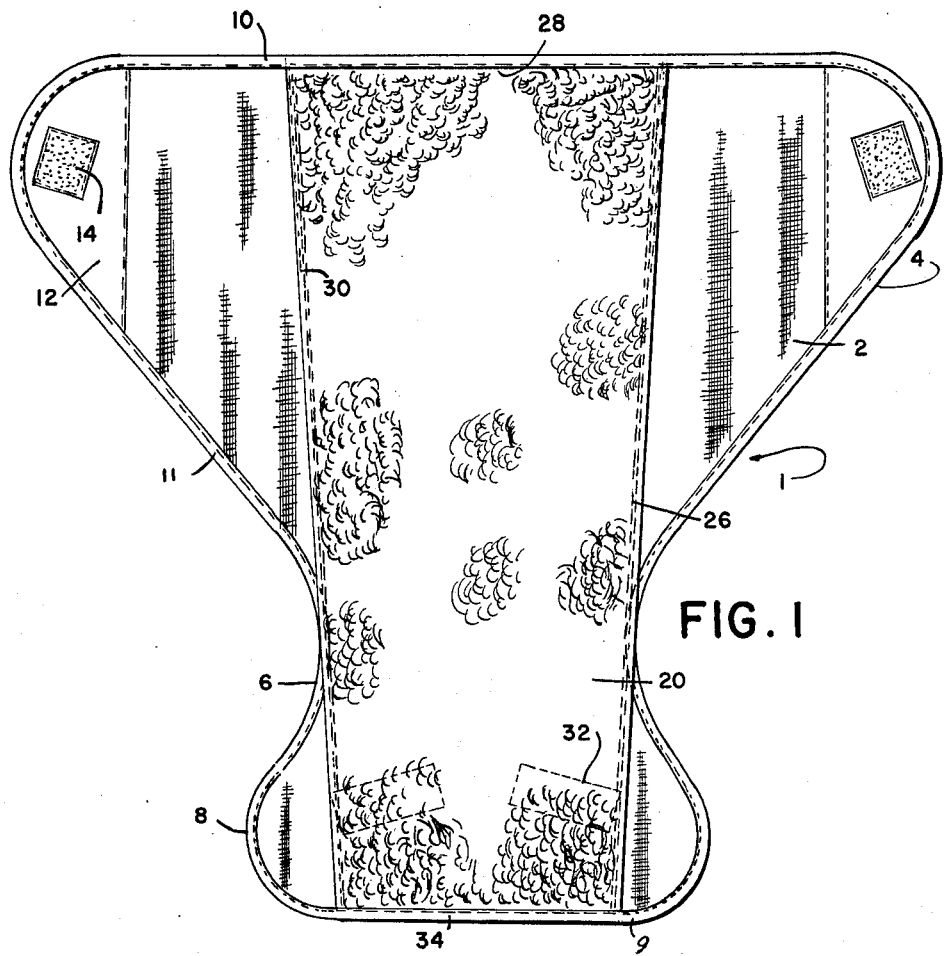
FIG. 1 illustrates a preferred embodiment of the invention, showing first and second panels.

Referring to FIG. 1, a garment which is a diaper cover type garment is generally indicated by the numeral 1. A first panel 2 has integrally formed back portion 4, medial portion 6 and front portion 8. A front edge 9 and a rear edge 10 of the first panel 2 are interconnected laterally by lateral edges 11.

As shown in FIG. 1, corner portions 12 which are preferably integrally formed portions of panel 2 have fasteners 14 mounted on inner surfaces.

Figure 2:
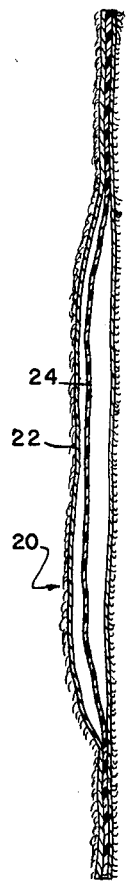
FIG. 2 is a side elevation partially in section, showing panels and layers of FIG. 1.

As shown in the detail of FIG. 2, a second panel 20 is connected to the first panel 2. The second panel 20 comprises an absorbent layer 22 joined around edges to a similarly shaped layer 24. The middle portions of layers 22 and waterproof layer 24 are loosely related.

Layers 22 and 24 of second panel 20 are stitched together at lateral edges 26. The rearward edge 28 of panel 20 is stitched to rearward edge 10 of the first panel 2. The forward edge 34 of the second panel is stitched to the forward edge 9 of the first panel.

In a preferred embodiment, stitches 30 join portions of the lateral edges of panel 20 to a rear portion 4 of first panel 2. The stitches 30 simply hold the panel 20 in appropriate alignment in the garment while in use.

Figure 3:
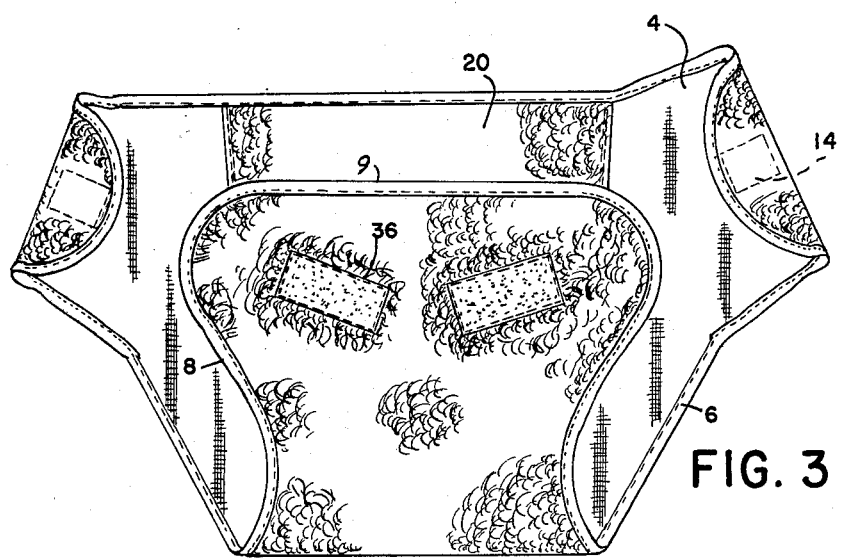
FIG. 3 is a view of the apparatus of FIG. 1, showing the folding of the apparatus into a body garment.

As further shown in FIG. 1 and FIG. 2, stitches 32 are provided through the first and second panels for holding fasteners 36 as shown in the FIG. 3. The relatively long strips of loop-type fasteners 36 are mounted on the front portion 8 of panel 2 at an angular relation to the forward edge 9 of the panel. The relatively short strips of hook-type fasteners 14 are fastened to loop-type fasteners 36 according to the body portion sizes of the wearer.

Figure 4:
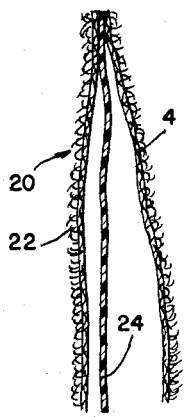
FIG. 4 is a partial cross-section of an alternate embodiment of the invention.

In the embodiment shown in FIGS. 1, 2 and 3, the panel 2 and layer 22 of panel 20 are formed of single-napped terry cloth in which the nap is on the outer surface of panel 2 and on the inner surface of layer 22 so that the naps face away from each other. A similar construction is shown in the FIG. 4 detail, which illustrates the back portion 4 of panel 2.

Figure 5:
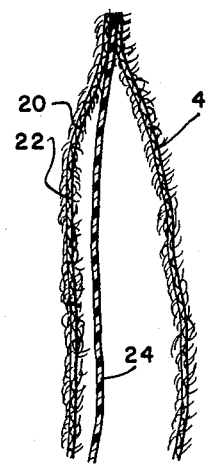
FIG. 5 is a partial cross-section of a further alternate embodiment of the invention.

In the detail shown in FIG. 5, a double faced terry cloth is employed with naps on both surfaces of the back portion 4 of panel 2 and layer 22 of panel 20.

Figure 6:
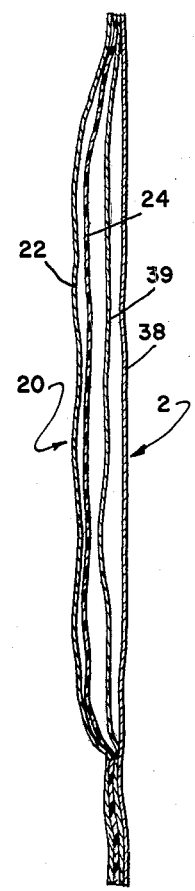
FIG. 6 is a side elevational detail, partially in cross-section of another embodiment of the invention.

In the FIG. 6 embodiment panel 2 is formed of two layers, 38 and 39, of fine knitted cotton jersey material. Layers 38 and 39 are joined at edges to form the panel 2. Panel 20 is formed of a waterproof layer 24 and a fine cotton flannel layer 22. Preferably the layers are joined only at rearward and forward edges, which are upper and lower edges as shown in FIG. 6. The modification shown in FIG. 6 is joined slightly above the lower or forward edge which is indicative of the through stitching of loop-type fasteners.

Figure 7:
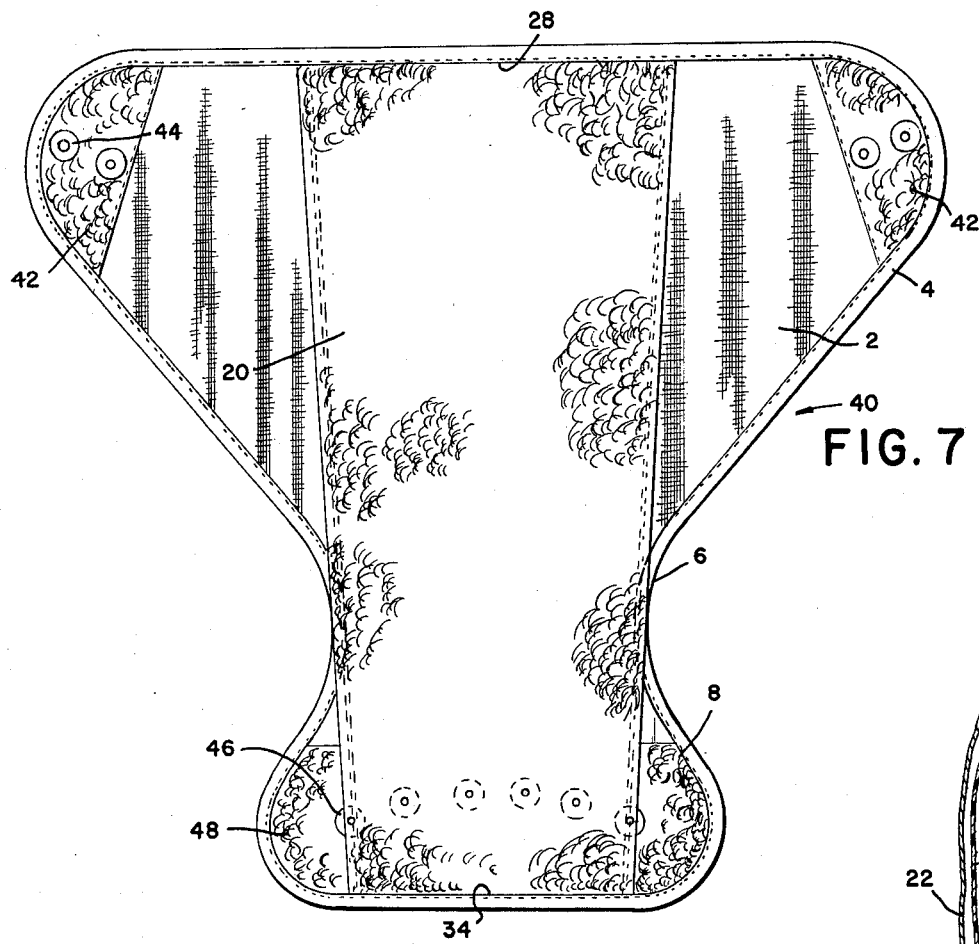
FIG. 7 is a detail of a further embodiment of the invention.

In FIG. 7 an alternate embodiment 40 is shown. Similar numbers are used to identify elements which are similar to those elements in the FIG. 1 embodiment. Reinforced rear corner panel sections 42 are stitched at edges to first panel 2. Snap-type fasteners 44 are mounted in the reinforcement panels 42 and the first panel 2 near intersections of the rearward edge and the lateral edges. Complementary snap-type fasteners 46 are mounted in a sloping pattern on the front portion 8 which is reinforced by a front portion reinforcement panel 48. The terry cloth reinforcement panel 48 is stitched around its edges to the panel 2.

While the invention has been described with reference to specific embodiments, it will be obvious to those skilled in the art that modifications and variations of the invention may be made without departing from the invention.

The scope of the invention is defined in the following claims.

We claim:

1. A garment comprising a first panel having a rearward edge and a forward edge and having lateral edges interconnecting the rearward and forward edges and further comprising a second panel having rearward and forward edges and having lateral edges interconnecting the rearward and forward edges of the second panel, the second panel being permanently attached to the first panel at rearward and forward edges with at least portions of the lateral edges of the second panel being spaced from the first panel, the second panel comprising a waterproof layer facing the first panel and a fabric layer facing away from the first panel, and means joining the first panel at positions near rearward and forward edges with an outer side of the first panel remote from the second panel whereby the first panel is formed and held as a garment with the second panel facing a body of the wearer, wherein the lateral edges of the first panel are sloped inward toward a medial portion of the first panel, thereby forming a medial narrow portion of the first panel, lateral edges of the second panel are substantially straight and the lateral edges of the second panel are positioned near medial inward portions of lateral edges of the first panel, and the second panel uniformly tapers inward from a major dimension on the rear edges to a lesser dimension on the front edges.

2. The garment of claim 1 wherein the first and second panels are longitudinally coextensive between the forward and rearward edges.

3. The garment of claim 1 wherein portions of lateral edges of the second panel are joined to the first panel near the rearward edge of the first panel.

4. The garment of claim 1 wherein portions of lateral edges of the second panel are positioned inward from portions of lateral edges of the first panel.

5. The garment of claim 1 wherein complementary fasteners are provided on an outer face of the first panel, positioned inward from the forward edge and wherein complementary fasteners are mounted on an inner face of the first panel near intersections of the rearward and lateral edges, whereby the garment is formed by covering the first panel about the second panel and covering rearward corners of the second panel over a forward portion of the first panel and joining the complementary fasteners.

6. The garment of claim 5 wherein the complementary fasteners comprise elongated strips of loop-type fasteners attached to one face of the first panel and relatively short strips of hook-type fasteners attached to another face of the first panel.

7. The garment of claim 6 wherein the relatively short strips of hook-type fasteners are connected to the corners of the inner face of the first panel and wherein the elongated loop-type fasteners are mounted on an outer face of the first panel in a sloped relationship to the forward edge.

8. The garment of claim 6 wherein the elongated strips of loop-type fasteners are mounted on the first panel and are connected to the first and second panels.

9. The garment of claim 5 further comprising a front reinforcing panel connected to the first panel along the front edge and between portions of the lateral edges and wherein fasteners are mounted on the first panel and are connected to the reinforcing panel, and further comprising corner reinforcing panels connected to the first panel at corners of the rearward and lateral edges and wherein the complementary fasteners are mounted in the first panel and are connected to the corner reinforcing portions.

* * * * *